United States Patent [19]
Wachter et al.

[11] Patent Number: 5,891,199
[45] Date of Patent: Apr. 6, 1999

[54] POLYMER DYESTUFFS AND THEIR USE FOR DYEING FIBRES

[75] Inventors: Rolf Wachter, Duesseldorf; Joerg Kahre, Monheim; David Rose, Hilden, all of Germany

[73] Assignee: Henkel Kommanditgesellschaft auf Aktien (KGaA), Duesseldorf, Germany

[21] Appl. No.: 913,709

[22] PCT Filed: Mar. 13, 1996

[86] PCT No.: PCT/EP96/01064

§ 371 Date: Sep. 30, 1997

§ 102(e) Date: Sep. 30, 1997

[87] PCT Pub. No.: WO96/29046

PCT Pub. Date: Sep. 26, 1996

[30] Foreign Application Priority Data

Mar. 22, 1995 [DE] Germany .................. 195 10 312.2

[51] Int. Cl.$^6$ .................. A61K 7/13; C09R 69/10
[52] U.S. Cl. .................. 8/403; 8/405; 8/647; 536/20
[58] Field of Search .................. 8/403, 405–435, 8/647; 536/20, 55.2

[56] References Cited

U.S. PATENT DOCUMENTS

| | | | |
|---|---|---|---|
| 3,993,789 | 11/1976 | Moll et al. | 426/250 |
| 4,228,259 | 10/1980 | Kalopissis et al. | 525/435 |
| 4,853,429 | 8/1989 | Sannan et al. | |
| 5,244,469 | 9/1993 | Shimoyama et al. | 8/438 |
| 5,442,048 | 8/1995 | Meister et al. | 536/20 |

FOREIGN PATENT DOCUMENTS

| | | |
|---|---|---|
| 0 382 150 | 8/1990 | European Pat. Off. . |
| 0 500 942 | 9/1992 | European Pat. Off. . |
| 2 361 447 | 3/1978 | France . |
| 24 61 642 | 5/1976 | Germany . |
| 27 36 266 | 2/1978 | Germany . |
| 04 085 367 | 3/1992 | Japan . |
| 1 009 911 | 11/1965 | United Kingdom . |
| WO 91/05808 | 5/1991 | WIPO . |

OTHER PUBLICATIONS

Chem. Abstracts 102(2):Abs. No. 8104g (Jan. 1985).
Happi 27:57 (1990).
Drug Cosm. Ind. 148:24 (1991).
Seifen–Öle–Fette–Washse 117:633 (1991).
The Chemistry of Synthetic Dyes, vol. V. (ed. K. Venkataraman) Academic Press, New York, 508–18 (1971).
J Falbe (ed.) "Surfactants in Consumer Products", Springer Verlag, Berlin, 54–124 (1987).
Cosm. Toil. 100: 77 (1985).

*Primary Examiner*—Margaret Einsmann
*Attorney, Agent, or Firm*—Ernest G. Szoke; Wayne C. Jaeschke; Glenn E. J. Murphy

[57] ABSTRACT

The proposal is for novel polymer dyestuffs obtained by condensing cationic biopolymers, e.g. chitosame, with dyestuffs which have a basic group, preferably a halogen function. The dyestuffs spread as a film on the fibers and can easily be washed out.

10 Claims, No Drawings

POLYMER DYESTUFFS AND THEIR USE FOR DYEING FIBRES

BACKGROUND OF THE INVENTION

1. Field of the invention

This invention relates to polymeric dyes obtained by condensation of cationic biopolymers with dyes, to a process for their production, to formulations containing these dyes for dyeing fibers, to processes for dyeing fibers using the polymeric dyes and to their use for dyeing fibers.

2. Discussion of the Related Art

So-called substantive dyes or oxidation dyes are normally used for coloring keratin fibers, preferably human hair. Oxidation dyes consist of a primary intermediate and a secondary intermediate and are formed on the hair itself under the effect of oxidizing agents or atmospheric oxygen.

However, there is a need on the market for coloring products which enable the color of hair to be rapidly changed, i.e. which can be quickly and completely washed out. The hair normally has to be washed 5 to 6 times to remove known products, something which many consumers find unsatisfactory.

Another disadvantage of known hair coloring or hair tinting formulations is that the products always penetrate into the keratin fibers and, hence, cause damage—albeit normally slight—to the hair structure. Since the formulations do not act selectively on keratin fibers, the treated scalp is generally colored at the same time which consumers also find undesirable.

Accordingly, the problem addressed by the present invention was to provide new formulations for the temporary coloring of keratin fibers which would not have any of the disadvantages mentioned above.

DESCRIPTION OF THE INVENTION

The present invention relates to polymeric dyes which are obtained by condensation of cationic biopolymers with dyes containing a leaving group. In one particularly advantageous embodiment of the invention, the cationic biopolymers used are chitosans while the dyes are those representatives which possess a halogen function as their leaving group.

It has surprisingly been found that dyes which have a suitable leaving group can readily be added to the nitrogen groups of cationic biopolymers. Whereas the cationic biopolymers themselves are generally colorless, the condensation products can range from yellow to blue in color, depending on the dye used. As solubility tests show, the coloring effect is not attributable to traces of dye dissolved in the polymer, but is a property of the new condensation products. The new polymeric dyes combine the properties of the cationic biopolymers with those of known dyes for coloring hair. This means that the dye does not act directly on the fibers, but instead is absorbed in the form of a uniform film. This affords the advantage of a much more gentle tint which is easy to wash out and does not affect the scalp.

The present invention also relates to a process for the production of polymeric dyes in which cationic biopolymers, preferably chitosans, are condensed with dyes which contain a leaving group, preferably a halogen function.

Cationic biopolymers

Among the most well-known and - according to the present invention—the most preferred cationic biopolymers are the chitosans which also belong to the group of hydrocolloids. Chemically, chitosans are partly deacetylated chitins varying in molecular weight which contain the—idealized—monomer unit (I):

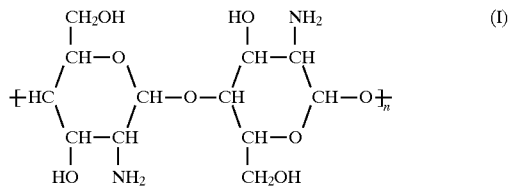

In contrast to most other hydrocolloids, chitosans are cationic biopolymers under physiological conditions. The positively charged chitosans are capable of interacting with oppositely charged surfaces and, accordingly, are used in cosmetic hair-care and body-care formulations and also as thickeners in amphoteric/cationic surfactant mixtures. Overviews of this subject have been published, for example, by B. Gesslein et al. in HAPPI 27, 57 (1990), by O. Skaugrud in Drug Cosm. Ind. 148, 24 (1991) and by E. Onsoyen et al. in Seifen-Öle-Fette-Wachse 117, 633 (1991). Chitosans are produced from chitin, preferably the shell remains of crustaceans which are available in large quantities as inexpensive raw materials. The chitin is normally first deproteinized by addition of bases, demineralized by addition of mineral acids and, finally, deacetylated by addition of strong bases, the molecular weights being distributed over a broad range. Corresponding processes for the production of—microcrystalline—chitosan are described, for example, in WO 91/05808 (Firextra Oy) and in EP-B1 0 382 150 (Hoechst).

Besides chitosans, chitosan derivatives, for example carboxymethyl chitosan or hydroxypropyl chitosan, may also be used as starting materials.

Another group of suitable cationic biopolymers of which the production has parallels to that of chitosan are obtained by (a) treating fresh crustacean shells with dilute aqueous mineral acid, (b) treating the resulting demineralized first intermediate product with aqueous alkali metal hydroxide solution, (c) retreating the resulting slightly deproteinized second intermediate product with dilute aqueous mineral acid and (d) finally treating the resulting decalcified third intermediate product with concentrated aqueous alkali metal hydroxide.

The cationic biopolymers obtainable by the process described above have a degree of deacetylation of 30 to 100 and preferably 60 to 98%. By virtue of their low ash content, they also have a particularly advantageous viscosity.

In the context of the present invention, cationic biopolymers are also understood to include related materials, for example gelatins, collagens and collagen degradation products.

Dyes

The present invention is based on the surprising observation that, basically, all dyes, i.e. chemical compounds which absorb in the visible light range and, accordingly, contain a chromophore, are suitable as reactants for the cationic biopolymers providing the molecule contains a suitable leaving group which allows addition or condensation, mainly with a nitrogen group of the biopolymer. Accordingly, the cationic biopolymer must satisfy the requirement that an adequate number of the nitrogen groups in the macro-molecule are not substituted.

Accordingly, suitable dyes are both the nitroaniline dyes widely used for coloring hair and the azo and anthraquinone dyes mainly used for dyeing textiles.

The dyes containing a suitable leaving group which are preferably used in accordance with the present invention are nitroaniline compounds substituted at the aromatic ring by at least one nitro group and one halogen atom.

Preferred dyes are nitroaniline compounds in which the amino group and the nitro group are in the ortho position or para position, which are substituted at the aromatic ring by an alkyl group containing 1 to 4 carbon atoms, in which the amino group is substituted by at least one alkyl, aminoalkyl, hydroxyalkyl, dihydroxyalkyl and/ or alkoxy group containing 1 to 15 carbon atoms and/or in which the amino group is part of a morpholine or piperidine ring.

Typical nitroaniline compounds which may be used as starting materials for the purposes of the present invention are, for example, 2-chloro-4-nitroaniline, 3-fluoro-4-nitroaniline, 2-nitro-4-bromoaniline, 4-chloro-3-nitro-1-(N-2-hydroxyethylamino)-benzene, 4-fluoro-2-nitro-1-(N,N-bis-2-hydroxyethylamino)-benzene, 4-fluoro-3-nitroaniline and 2-chloro-6-methyl-3-nitro-aniline. Other substitution patterns for suitable aniline compounds can be found in "The Chemistry of Synthetic Dyes", Vol. V (ed. K. Venkataraman), Academic Press, New York/London, 1971, pages 508–518.

Condensation reaction

The reaction of the cationic biopolymers with the dyes is a simple condensation between a nitrogen function of the biopolymer and the leaving group of the dye. If the leaving group is chloride, for example, the reaction between the two components is accompanied by the elimination of hydrogen chloride which may be bound in the molecule as an adduct via a basic nitrogen group.

The cationic biopolymers and the dyes are normally used in a stoichiometric ratio of about 1:1, the molar quantity of dye used being based on the molecular weight of the nitrogen groups in the biopolymer. The reaction preferably takes place under reflux in the presence of a basic compound, for example potassium carbonate or sodium carbonate, in an organic solvent, for example ethanol, over a period of 1 to 12 h and typically 5 to 8 h. It is then advisable to separate the condensation product from the mother liquor and to subject it to careful washing and drying. The yield of normally crystalline addition products is substantially quantitative.

Commercial Applications

The present invention also relates to formulations for the temporary coloring of fibers, preferably keratin fibers, which contain the polymeric dyes mentioned above. To produce these formulations, the polymeric dyes may be incorporated, for example, in a suitable water-containing carrier. For hair coloring purposes, such carriers are, for example, cremes, emulsions, gels or even surfactant-containing foaming solutions, for example shampoos, foam aerosols or other preparations suitable for application to the hair.

Surfactants

The coloring formulations according to the invention may additionally contain any of the active substances, additives and auxiliaries known in such formulations. In many cases, the coloring formulations contain at least one surfactant. In principle, both anionic and zwitterionic, ampholytic, non-ionic and cationic surfactants are suitable.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl glutamates, acyl tartrates, alkyl oligoglucoside sulfates, protein fatty acid condensates (especially wheat-based vegetable products) and alkyl (ether) phosphates. Where the anionic surfactants contain polyglycol ether chains, they may have a conventional homolog distribution, although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid-N-alkyl glucamides, protein hydrolyzates (especially wheat-based vegetable products), polyol fatty acid esters, sugar esters, sorbitan esters and polysorbates. If the nonionic surfactants contain polyglycol ether chains, they may have a conventional homolog distribution, although they preferably have a narrow homolog distribution.

Typical examples of cationic surfactants are quaternary ammonium compounds and esterquats, more particularly quaternized fatty acid trialkanolamine ester salts.

Also suitable for the purposes of the invention are cationic silicone oils, for example the commercially available products Q2-7224 (manufacturer: Dow Corning; a stabilized trimethyl silyl amodimethicone) Dow Corning 929 Emulsion (containing a hydroxylamino-modified silicone which is also known as Amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethylamine obtainable under the name of Tego Amid® S 18, are distinguished not only by a favorable conditioning effect, but also and in particular by their ready biodegradability.

Typical examples of amphoteric and zwitterionic surfactants are alkyl betaines, alkyl amidobetaines, aminopropionates, aminoglycinates, imidazolinium betaines and sulfobetaines.

The surfactants mentioned are all known compounds. Particulars of their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöadditive", Thieme Verlag, Stuttgart, 1978, pages 123 to 217.

Auxiliaries and additives

The formulations according to the invention may contain emulsifiers, superfatting agents, thickeners, biogenic agents, film formers, preservatives, dyes and fragrances as further auxiliaries and additives.

Suitable emulsifiers are both known w/o and o/w emulsifiers, for example hydrogenated and ethoxylated castor oil, polyglycerol fatty acid esters or polyglycerol polyricinoleates or polyglycerol poly-12-hydroxy-stearates.

Suitable superfatting agents are such substances as, for example, polyethoxylated lanolin derivatives, lecithin derivatives, polyol fatty acid esters, monoglycerides and fatty acid alkanolamides, the latter also serving as foam stabilizers.

Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates, polyvinyl alcohol and polyvinyl pyrrolidone, surfactants, for example narrow-range fatty alcohol ethoxylates or alkyl oligoglucosides, and electrolytes, such as sodium chloride and ammonium chloride.

Biogenic agents in the context of the invention are, for example, plant extracts and vitamin complexes.

Typical film formers are, for example, quaternized chitosan, polyvinyl pyrrolidone, vinyl pyrrolidone/vinyl acetate copolymers, polymers of the acrylic acid series, quaternary cellulose derivatives, collagen, hyaluronic acid or salts thereof and similar compounds.

Suitable preservatives are, for example, phenoxyethanol, formaldehyde solution, parabens, pentanediol or sorbic acid.

The total content of auxiliaries and additives may be from 1 to 50% by weight and is preferably from 5 to 40% by weight, based on the particular formulation.

The present invention also relates to a process for temporarily coloring keratin fibers, in which the fibers are treated with the polymeric dyes according to the invention. The polymeric dyes may be applied during washing of the hair but are preferably applied by working in with a comb.

Although the polymeric dyes according to the invention may be used with advantage for coloring or tinting hair, it has also been found that the dyes are absorbed by synthetic fibers, for example polyacrylic fibers, polyester fibers, polyamide fibers and even by rayon. Accordingly, the present invention also relates to a process for dyeing synthetic textile fibers in which the fibers are treated with the polymeric dyes according to the invention.

Finally, the present invention relates to the use of the polymeric dyes according to the invention for the temporary coloring of fibers, preferably keratin fibers. The polymeric dyes are normally used in the form of 1% by weight solutions. By contrast, the concentration of dyes in the formulations may be from 0.001 to 0.1% by weight, based on the mixture as a whole.

The following Examples are intended to illustrate the invention without limiting it in any way.

EXAMPLES

I. Production Examples

Example 1

Reaction of chitosan with 4-fluoro-3-nitroaniline. In a 250 ml three-necked flask equipped with a stirrer and reflux condenser, 2.5 g (0.01375 mole, based on nitrogen) of chitosan, 2.15 g (0.01375 mole) of 4-fluoro-3-nitroaniline and 1.86 g (0.01375 mole) of water-free potassium carbonate were dissolved in 150 ml of ethanol. The mixture was heated under reflux for 7 h and, after cooling, the solid formed was filtered off under suction from the yellow mother liquor through a frit. In order to remove 4-fluoro-3-nitroaniline still present, the crystals were then washed with quantities of 50 ml of hot ethanol until the ethanol remained colorless. The residue was then washed with water and once more with hot ethanol to remove inorganic salts and, finally, was dried at 70° C. to constant weight. 4.5 g of an orange-yellow colored crystalline chitosan derivative were obtained.

Example 2

Reaction of chitosan with 2-chloro-6-methyl-3-nitroaniline. In a 250 ml three-necked flask equipped with a stirrer and reflux condenser, 2.5 g (0.01375 mole, based on nitrogen) of chitosan, 2.15 g (0.01375 mole) of 2-chloro-6-methyl-3-nitroaniline and 1.86 g (0.01375 mole) of water-free potassium carbonate were dissolved in 150 ml of ethanol. The mixture was heated under reflux for 7 h and, after cooling, the solid formed was filtered off under suction from the mother liquor through a frit. To remove any 2-chloro-6-methyl-3-nitroaniline still present, the crystals were then washed with quantities of 50 ml of hot ethanol until the ethanol remained colorless. The residue was then washed with water and once more with hot ethanol to remove inorganic salts and, finally, was dried at 70° C. to constant weight. 4.5 g of a crystalline chitosan derivative were obtained.

II. Formulation Examples

Typical examples of basic formulations for hair-cosmetic products which may contain the new polymeric dyes as 1% by weight solutions in quantities of 10 to 50% by weight can be found in "Hair Treatment Products Formulary" in Cosm. Toil. 100, 77 (1985), of which the teaching is hereby specifically included as part of the present disclosure. In the following Examples, a "polymeric dye" is understood to be a condensation product according to Example 1 in the form of a 1% by weight solution.

| 1. Leave-on coloring hair rinse | |
|---|---|
| Sepigel ® 305 | 3.0% by weight |
| Nutrilan ® I-50 | 2.0% by weight |
| Dehyquart ® A | 0.8% by weight |
| Plantaren ® 1200 | 0.5% by weight |
| Cetiol ® J 600 | 0.5% by weight |
| Ethanol | 10.0% by weight |
| Polymeric dye | 30.0% by weight |
| Glycerol, 86% by weight | 5.0% by weight |
| Water, preservative | to 100 |
| 2. Coloring hair styling spray | |
| Cetiol ® OE | 5.0% by weight |
| Cetiol ® LC | 5.0% by weight |
| Emulgade ® SE | 4.5% by weight |
| Eumulgin ® B2 | 1.0% by weight |
| Polymeric dye | 50.0% by weight |
| Water, preservative | to 100 |
| 3. Coloring hair styling spray | |
| Cetiol ® OE | 5.0% by weight |
| Cetiol ® LC | 5.0% by weight |
| Emulgade ® SE | 4.5% by weight |
| Eumulgin ® B2 | 1.0% by weight |
| Polymeric dye | 50.0% by weight |
| Water, preservative | to 100 |

TABLE 1

Trade names and CTFA names

| Trade Name | | CTFA Name |
|---|---|---|
| Cetiol | J 600 | Oleyl Erucate |
| | LC | Coco Caprylate Caprate |
| | OE | Dicapryl Ether |
| Dehyquart | A | Cetrimmonium Chloride |
| Emulgade | SE | Glyceryl Stearate (and) Ceteareth-20 (and) Ceteareth-12 (and) Cetearyl Alcohol (and) Cetyl Palmitate |
| Eumulgin | B2 | Ceteareth-20 |
| Nutrilan | I-50 | Hydrolyzed Collagen |
| Plantaren | 1200 | Lauryl Polyglucose |

We claim:

1. A polymeric dye comprising a condensation product of a chitosan with a halogen-substituted nitroaniline compound.

2. A polymeric dye according to claim 1 wherein the nitroaniline compound is a halogen-substituted 2-nitroaniline or 4-nitroaniline, and substituted by an alkyl group having 1 to 4 carbon atoms and wherein the amino group of the nitroaniline is substituted by a group having 1 to 15 carbon atoms selected from the group consisting of alkyl, aminoalkyl, hydroxyalkyl, dihydroxyalkyl, and alkoxy.

3. A polymeric dye according to claim 1 wherein the nitroaniline compound is a halogen-substituted 2-nitroaniline or 4-nitroaniline, and substituted by an alkyl group having 1 to 4 carbon atoms and wherein the amino group of the nitroaniline forms part of a morpholine or piperidine ring.

4. A polymeric dye according to claim 2 wherein the halogen-substituted nitroaniline compound is selected from the group consisting of a halogen-substituted 2-chloro-4- a halogen-substituted nitroaniline, 3-fluoro-4-nitroaniline, 2-nitro-4-bromoaniline, 4-chloro-3-nitro-1-(N-2-hydroxyethylamino)-benzene, 4-fluoro-2-nitro-1-(N,N-bis-2 hydroxyethylamino)-benzene, 4-fluoro-3-nitroaniline, and 2-chloro-6-methyl-3-nitroaniline.

5. Formulations for the temporary coloring of fibers containing the polymeric dyes claimed in claim 1.

6. A process for the temporary coloring of keratin fibers, in which the fibers are dyed with the polymeric dyes claimed in claim 1.

7. A process for the temporary dyeing of synthetic textile fibers, in which the fibers are dyed with the polymeric dyes claimed in claim 1.

8. A process for preparing a polymeric dye comprising condensing in an organic solvent in the presence of a base a chitosan compound and a halogen-substituted ortho- or para-nitroaniline compound substituted by an alkyl group having 1 to 4 carbon atoms in a molar ratio of 1:1, wherein said molar ratio represents the ratio of moles of dye to moles of nitrogen groups in the chitosan.

9. A process according to claim 8, wherein the amino group of the nitroaniline compound is substituted by a group having 1 to 15 carbon atoms selected from the group consisting of alkyl, aminoalkyl, hydroxyalkyl, dihydroxyalkyl, and alkoxy.

10. A process according to claim 8, wherein the amino group of the nitroaniline compound forms part of a morpholine or piperidine ring.

* * * * *